United States Patent

Kishimoto et al.

[11] 4,447,436
[45] * May 8, 1984

[54] 1,2,3,4-TETRAHYDROISOQUINOLINES 6.10,7,8 DIHYDROXY SUBSTITUTE-1-METHYLANILINO AND USE AS SMOOTH MUSCLE RELAXANTS

[75] Inventors: Teiji Kishimoto, Kawanishi; Hiromu Kochi, Sakai; Masayuki Kato, Ikeda, all of Japan

[73] Assignee: Fujisawa Pharmaceutical Co., Ltd., Osaka, Japan

[ * ] Notice: The portion of the term of this patent subsequent to Sep. 2, 1997 has been disclaimed.

[21] Appl. No.: 109,531

[22] Filed: Jan. 4, 1980

Related U.S. Application Data

[62] Division of Ser. No. 628,935, Nov. 5, 1975, Pat. No. 4,220,647.

[30] Foreign Application Priority Data

Nov. 6, 1974 [JP] Japan ................................ 49-128479
Nov. 15, 1974 [JP] Japan ................................ 49-132287
Dec. 12, 1974 [JP] Japan ................................ 49-143293

[51] Int. Cl.³ .................... A61K 31/47; C07D 217/04
[52] U.S. Cl. .................................. 424/258; 546/146; 546/150
[58] Field of Search ................ 546/146, 150; 424/258

[56] References Cited

U.S. PATENT DOCUMENTS

| | | | |
|---|---|---|---|
| 3,378,561 | 4/1968 | Montzka | 546/147 |
| 3,389,140 | 6/1968 | Montzka | 546/148 |
| 3,846,432 | 11/1974 | Tanaka et al. | 546/150 |
| 4,220,647 | 9/1980 | Kishimoto et al. | 546/150 |

Primary Examiner—Paul M. Coughlan, Jr.
Assistant Examiner—David B. Springer
Attorney, Agent, or Firm—Oblon, Fisher, Spivak, McClelland & Maier

[57] ABSTRACT

1,2,3,4-Tetrahydroisoquinolines having the formula:

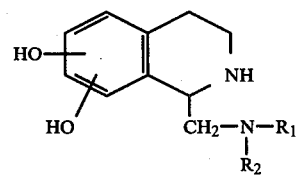

wherein $R_1$ and $R_2$ are each hydrogen, lower alkyl, lower alkenyl, acyl, aryl or ar(lower)alkyl, in which aryl and the aryl moiety of the ar(lower)alkyl may contain at least one substituent selected from the group consisting of halogen, lower alkoxy, amino, nitro, hydroxy, acyloxy, ar(lower)alkoxy, lower alkylenedioxy, halo(lower)alkyl, acylamino, ar(lower)alkylamino and aryl, and pharmaceutically acceptable salts thereof, having a relaxant activity on smooth muscles.

5 Claims, No Drawings

1,2,3,4-TETRAHYDROISOQUINOLINES 6,10,7,8 DIHYDROXY SUBSTITUTE-1-METHYLANILINO AND USE AS SMOOTH MUSCLE RELAXANTS

This is a division, of application Ser. No. 628,935, filed Nov. 5, 1975 U.S. Pat. No. 4,220,647 issued Sept. 9, 1980.

BACKGROUND OF THE INVENTION

Field of the Invention

The present invention relates to new 1,2,3,4-tetrahydroisoquinolines and the pharmaceutically acceptable salts thereof, which have a relaxing activity on smooth muscles, and or processes for the preparation thereof.

SUMMARY OF THE INVENTION

The new 1,2,3,4-tetrahydroisoquinolines of the present invention are represented by the formula:

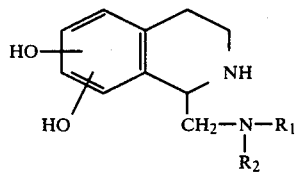

wherein $R_1$ and $R_2$ are each hydrogen, lower alkyl, lower alkenyl, acyl, aryl or ar(lower)alkyl, in which the aryl groups and the aryl moiety of the ar(lower)alkyl may have substituent(s) selected from the group consisting of halogen, lower alkoxy, amino, nitro, hydroxy, acyloxy, ar(lower)alkoxy, lower alkylenedioxy, halo(lower)alkyl, acylamino, ar(lower)alkylamino and aryl.

DESCRIPTION OF THE PREFERRED EMBODIMENTS

In this specification, it is to be understood that the term "lower" as used in connection with the moieties derived from alkane or alkene such as alkyl or alkenyl is intended to mean a group having 1 to 6 carbon atom(s) unless otherwise indicated.

Suitable lower alkyl groups include those having 1 to 6 carbon atom(s). These may be branched. Typical examples are methyl, ethyl, propyl, isopropyl, butyl, isobutyl, tertbutyl, pentyl or hexyl.

Suitable lower alkenyl groups include those having 2 to 6 carbon atoms such as vinyl, 1-propenyl, allyl, isopropenyl, 2-butenyl, 3-pentenyl or 4-hexenyl.

Suitable acyl groups and acyl moieties of the acyloxy and acylamino groups include lower alkanoyl (e.g., formyl, acetyl, propionyl, etc.); mono (or di or tri) halo(lower)alkanoyl (e.g., chloro acetyl, trifluoroacetyl, etc.); ar(lower)alkanoyl, for example, phenyl(lower)alkanoyl (e.g., phenylacetyl, phenylpropionyl, etc.) or the like; ar(lower)alkoxycarbonyl which may have suitable substituent(s), for example, phenyl(lower)alkoxycarbonyl (e.g., benzyloxycarbonyl, phenethyloxycarbonyl, phenylpropyloxycarbonyl, etc.), halophenyl(lower)alkoxycarbonyl (e.g., 2-bromobenzyloxycarbonyl, 4-chlorobenzyloxycarbonyl, 4-bromobenzyloxycarbonyl, etc.), nitrophenyl(lower)alkoxycarbonyl (e.g., 4-nitrobenzyloxycarbonyl, etc.), mono(or di)-(lower)alkoxyphenyl(lower)alkoxycarbonyl (e.g., 4-methoxybenzyloxycarbonyl, 3,4-dimethoxybenzyloxy carbonyl, etc.), phenylazophenyl(lower)alkoxycarbonyl (e.g., 4-(phenylazo)benzyloxycarbonyl, etc.), or the like; lower alkoxycarbonyl (e.g., methoxycarbonyl, ethoxycarbonyl, isopropoxycarbonyl, 1-cyclopropylethoxycarbonyl, tertbutoxycarbonyl, 1,1-dimethylpropoxycarbonyl, etc.); mono (or di or tri) halo(lower)alkoxycarbonyl (e.g., trichloroethoxycarbonyl, tribromoethoxycarbonyl, etc.); aroyl having 7 or 8 carbon atoms (e.g., benzoyl, toluoyl, etc.); lower alkanesulfonyl (e.g., mesyl, ethanesulfonyl, propanesulfonyl, etc.); arenesulfonyl having 6 or 7 carbon atoms (e.g., benzenesulfonyl, tosyl, etc.); 8-quinolyloxycarbonyl; 2-pyridylmethoxycarbonyl; adamantyloxycarbonyl; and the like.

Suitable aryl groups include those having 6 to 10 carbon atoms such as phenyl, phenyl having lower alkyl (e.g., tolyl, xylyl, mesityl, cumenyl, etc.) or naphthyl, and preferably those having 6 or 7 carbon atoms.

Suitable ar(lower)alkyl groups include those having 7 to 13 carbon atoms such as phenyl(lower)alkyl (e.g., benzyl, phenethyl, etc.), tolylmethyl, xylylmethyl, cumenylmethyl or diphenylmethyl, and preferably those having 7 or 8 carbon atoms.

Suitable halogens include chlorine, bromine, fluorine and iodine.

Suitable lower alkoxy groups include those having 1 to 6 carbon atom(s) such as methoxy, ethoxy, propoxy, isopropoxy, butoxy, isobutoxy, tert-butoxy, pentyloxy or hexyloxy, and preferably those having 1 to 4 carbon atom(s), and more preferably those having 1 or 2 carbon atom(s).

Suitable ar(lower)alkoxy groups include those having 7 to 10 carbon atoms such as phenyl(lower)alkoxy (e.g., benzyloxy, phenethyloxy, etc.), tolylmethyloxy, xylylmethyloxy or cumenylmethyloxy, and preferably those having 7 to 8 carbon atoms.

Suitable loweralkylenedioxy groups include those having 1 or 2 carbon atom(s) such as methylenedioxy or ethylenedioxy.

Suitable halo(lower)alkyl groups include those having 1 to 6 carbon atom(s) such as mono(or di or tri) halo(lower)alkyl (e.g., chloromethyl, chloroethyl, bromoethyl, dichloroethyl, trichloromethyl, trifluoromethyl, trichloroethyl, iodopropyl, chloropentyl, chlorohexyl, etc.), or the like, and preferably those having 1 to 4 carbon atom(s), and more preferably those having 1 or 2 carbon atom(s).

Suitable ar(lower)alkylamino groups include amino groups having the aforementioned ar(lower)alkyl groups thereon.

Sutable acyloxy, acylamino and aryl substituents are as defined above.

The above-mentioned aryl groups and the aryl moiety of the ar(lower)alkyl groups for $R_1$ and $R_2$ may have at least one, preferably one to three, substituent(s) as mentioned above. When said aryl group or aryl moiety has more than two substituents, said substituents may be the same or different. When the aforementioned substituents on the aryl and the aryl moieties of the ar(lower)alkyl possibilities for $R_1$ and $R_2$ are ar(lower)alkoxy and/or ar(lower)alkylamino, the aryl and the aryl moieties of these substituents may further be substituted with the aforementioned halogen and/or lower alkoxy groups at desired positions.

Suitable pharmaceutically acceptable salts include salts with an acid, such as an inorganic acid (e.g., hydrochloric acid, hydrobromic acid, sulfuric acid, phosphoric acid, etc.) or an organic acid (e.g., acetic acid, tartaric acid, fumaric acid, maleic acid, toluenesulfonic acid, camphorsulfonic acid, etc.)

According to the present invention, the object compounds (I) can be prepared by various methods, which are described as follows:

1. One process is represented by the following scheme:

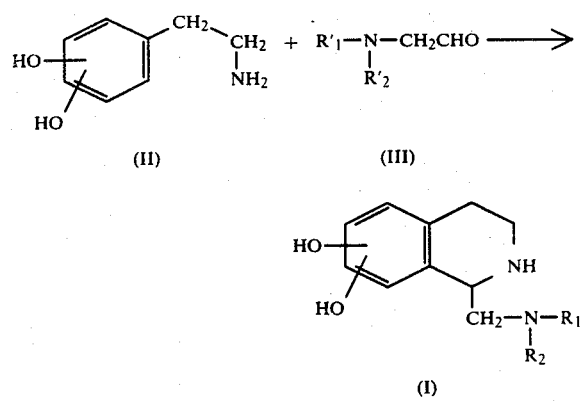

wherein R'₁ and R'₂ are each hydrogen, lower alkyl, lower alkenyl, acyl, aryl or ar(lower)alkyl, in which the aryl and the aryl moieties of the ar(lower)alkyl may have substituent(s) selected from the group consisting of halogen, lower alkoxy, amino, nitro, hydroxy, acyloxy, ar(lower)alkoxy, lower alkylenedioxy, halo(lower)alkyl, acylamino, ar(lower)alkylamino and aryl, and R₁ and R₂ are each as defined above.

The present reaction can be carried out by reacting the compound (II) or a salt thereof with the aldehyde compound (III) or a reactive equivalent thereof.

The compound (II) has two hydroxy groups at any two positions between the second and sixth position of the benzene ring, but does not have the two hydroxy groups at the second and sixth positions, simultaneously.

Suitable salts of the compound (II) include inorganic acid salts (e.g., hydrochlorides, hydrobromides, sulfates, carbonates, etc) and organic acid salts (e.g., acetates, oxalates, p-toluenesulfonates, tartarates, fumarates, maleates, etc.)

Reactive equivalents of the compound (III) include all compounds capable of serving the same purpose as does compound (III) in this reaction. Suitable such reactive equivalents include those having (a) a derivative on the formyl group of the compound (III) such as acetal, hemiacetal, hydrate(diol), mono or diacylated diol, thioacetal, hemithioacetal, Schiff's base, oxime, semicarbazone, thiosemicarbazone, alkoxalyl (e.g., methoxalyl, ethoxalyl, etc.) or the like; (b) compounds wherein the formylmethylene group of the aldehyde compound (III) is in the form of 2-acyloxyvinyl (e.g., 2-acetoxyvinyl, 2-propionyloxyvinyl, etc.), 2-lower alkoxyvinyl (e.g., 2-methoxyvinyl, 2-ethoxyvinyl, 2-propoxyvinyl, 2-isopropoxyvinyl, etc.), 2-lower alkylthiovinyl (e.g., 2-methylthiovinyl, 2-ethylthiovinyl, 2-propylthiovinyl, etc.), 2-aminovinyl; and (c) compounds substituted by a carboxy group or a derivative (z) thereof, for one hydrogen atom on the methylene group adjacent to the formyl group of the compound (III) or reactive equivalents thereof as mentioned in (a) or (b) above.

Suitable such derivatives (z) of the carboxy group include esters such as a saturated or unsaturated, cyclic or acyclic aliphatic hydrocarbon esters (e.g., methyl ester, ethyl ester, propyl ester, isopropyl ester, butyl ester, t-butyl ester, cyclohexyl ester, cycloheptyl ester, vinyl ester, 1-propenyl ester, 2-propenyl ester, 3-butenyl ester, etc.), aryl esters (e.g., phenyl ester, xylyl ester, tolyl ester, naphthyl ester, etc.), aralkyl esters (e.g., benzyl ester, phenethyl ester, etc.) or the like; amides such as N-lower alkyl amide (e.g., N-methyl amide, N-ethyl amide, etc.), a N-aryl amide (e.g., N-phenyl amide, etc.), a N,N-di(lower alkyl)amide (e.g., N,N-dimethyl amide, N,N-diethylamide, N-ethyl-N-methyl amide, etc.), or other amides with imidazole, 4-substituted imidazole, etc. or the like; and anhydrides such as a mixed anhydride with a dialkylphosphoric acid, dibenzylphosphoric acid, a halogenated phosphoric acid, a dialkylphosphorous acid, sulfurous acid, thiosulfuric acid, sulfuric acid, an alkylcarbonic acid, an aliphatic carboxylic acid (e.g., pivalic acid, pentanoic acid, isopentanoic acid, 2-ethylbutanoic acid, chloroacetic acid, etc.), or an aromatic carboxylic acid (e.g., benzoic acid, etc.); and symmetrical anhydrides.

The present reaction can be also carried out in the presence of an acid. Suitable acids include, for example, an inorganic acid (e.g., hydrochloric acid, hydrobromic acid, sulfuric acid, phosphoric acid, etc.) and an organic acid (e.g., acetic acid, chloroacetic acid, trifluoroacetic acid, propionic acid, methanesulfonic acid, etc.). The reaction can be carried out with or without a solvent. Suitable solvents include, for example, methanol, ethanol, n-butanol, water, benzene, chloroform, dioxane, a buffer solution and the like, and mixtures thereof. The reaction temperature is not critical. The reaction can be carried out at low or elevated temperature, most usually at ambient temperature, or, using heating, at a temperature around the boiling point of the solvent.

When isoquinoline rings are formed in the present reaction, it sometimes occurs that the direction of ring closure varies. Consequently, occasionally, hydroxy group position isomers of the isoquinoline ring are obtained. These products are also included in the scope of the present invention. Furthermore, when R'₁ and R'₂ are acyl or when the substituents on the aryl and the ar(lower)alkyl alternatives for R'₁ and R'₂ are acyloxy or acylamino, these substituents may be converted into hydrogen, hydroxy and amino, respectively, in the course of the reaction. Such products are also included in the scope of the present invention.

2. An alternative process for preparing the compounds of this invention is represented by the following scheme:

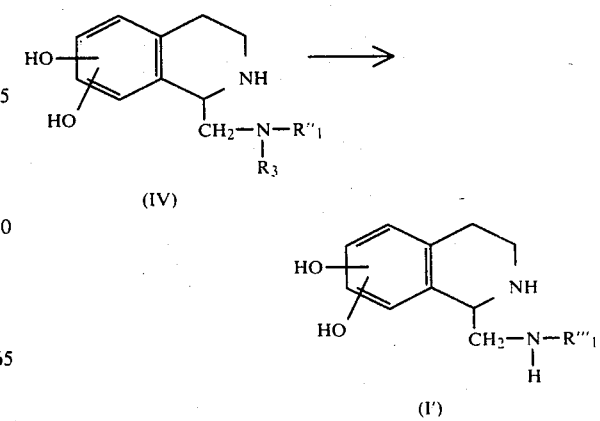

wherein R"₁ is hydrogen, lower alkyl, lower alkenyl, a protective group for an amino or aryl which may have substituent(s) selected from the group consisting of halogen, lower alkoxy, amino, nitro, hydroxy, acyloxy, ar(lower)alkoxy, lower alkylenedioxy, halo(lower)alkyl, acylamino, ar(lower)alkylamino and aryl, $R_3$ is a protective group for an amino and R"'₁ is hydrogen, lower alkyl, lower alkenyl or aryl which may have substituent(s) selected from the group consisting of halogen, lower alkoxy, amino, nitro, hydroxy, acyloxy, ar(lower)alkoxy, lower alkylenedioxy, halo(lower)alkyl, acylamino, ar(lower)alkylamino and aryl.

In this reaction, the compound (IV) or a salt thereof is subjected to elimination of the protective group(s) for the amino to give the compound (I').

Suitable protective groups for the amino include both protective groups for primary amino and secondary amino groups. They include the aforementioned acyl group, and further include conventional protective groups for amino other than the acyl group such as ar(lower)alkyl (e.g., benzyl, phenethyl, trityl, etc.), substituted phenylthio(e.g., 2-nitrophenylthio, 2,4-dinitrophenylthio, etc.) lower alkoxy- or ar(lower)alkoxy(lower)alkyl (e.g., methoxymethyl, benzyloxymethyl, etc.), tetrahydropyranyl, substituted or unsubstituted benzylidene (e.g., 2-hydroxybenzylidene, benzylidene, 4-nitrobenzylidene, 2-hydroxy-5-chlorobenzylidene, etc.), substituted lower alkylene (e.g., 2-hydroxy-1-naphthylmethylene, 3-hydroxy-4-pyridylmethylene, etc.), acyl substituted lower alkylidene (e.g., 1-methoxycarbonyl-2-propylidene, 1-ethoxycarbonyl-2-propylidene, 3-ethoxycarbonyl-2-butylidene, 1-acetyl-2-propylidene, 1-benzoyl-2-propylidene, 1-[N-(2-methoxyphenyl)carbamoyl]-2-propylidene, 1-[N-(4-methoxyphenyl)carbamoyl]-2-propylidene, etc.), acyl substituted cyclo(lower)alkylidene (e.g., 2-ethoxycarbonylcyclohexylidene, 2-ethoxycarbonylcyclopentylidene, 2-acetylcyclohexylidene, etc.), 3,3-dimethyl-4-oxocyclohexylidene (in these groups, for example, 1-methoxycarbonyl-2-propylidene and 2-ethoxycarbonylcyclohexylidene can also be represented as 1-methoxycarbonyl-1-propen-2-yl and 2-ethoxycarbonyl-1-cyclohexenyl, respectively), di- or tri(lower)alkylsilyl or the like. Suitable protective groups for the amino in the present reaction are not limited to the groups mentioned above but include all conventional protective groups for an amino which are eliminable in the present reaction.

Suitable salts of the compound (IV) include those listed for the compound (II).

The elimination of the protective group(s) for the amino is conducted in a conventional manner well known in the art, for example, by hydrolysis using an acid or a base, or by reduction of the compound (IV) or a salt thereof. Of course, it is to be understood that approximate reaction conditions for eliminating the protective groups for the amino will vary depending upon the kind of protective group used. When the protective groups are, for example, groups such as acetyl, benzyl, ar(lower)alkoxycarbonyl (e.g., benzyloxycarbonyl), substituted ar(lower)alkoxycarbonyl, lower alkoxycarbonyl, substituted lower alkoxycarbonyl, tosyl, adamantyloxycarbonyl, trityl, methoxymethyl, substituted phenylthio or the like, the protective groups may be eliminated by hydrolysis using an acid, for example, an inorganic acid such as hydrohalogenic acid (e.g., hydrobromic acid, hydrochloric acid, etc.), or an organic acid such as substituted or unsubstituted lower alkanoic acid (e.g., formic acid, acetic acid, trifluoroacetic acid, etc.), or a mixture thereof, or the like. The elimination takes place easily under reduced pressure. The hydrolysis using an acid can be also carried out in a solvent such as water, a hydrophilic organic solvent or a mixture thereof. When the protective groups are acyl groups, the protective groups may be eliminated by hydrolysis using a base. Suitable bases include inorganic bases, for example, alkaline metal hydroxides such as alkali metal hydroxides (e.g., sodium hydroxide, potassium hydroxide, etc.), alkaline earth metal hydroxides (e.g., magnesium hydroxide, calcium hydroxide, etc.), alkali metal or alkaline earth metal carbonates, or alkali metal bicarbonates, and organic bases such as trialkylamines (e.g., trimethylamine, triethylamine, etc.), picoline, N-methylpyrrolidine or N-methylmorpholine, and the like. The hydrolysis using a base is preferably carried out in a solvent such as water, a hydrophilic solvent or a mixture thereof. When the protective group is trifluoroacetyl, it can be easily eliminated only by treating the compound (IV) or the salt thereof with an aqueous alkaline solution such as sodium bicarbonate aqueous solution. When the protective group is for example a group such as benzyloxycarbonyl, substituted benzyloxycarbonyl, trichloroethoxycarbonyl, 2-pyridylmethoxycarbonyl, diphenylmethoxycarbonyl, benzyl, trityl or the like, the protective group may be eliminated by reduction. Suitable methods of reduction include the use of a metal (e.g., tin, zinc, etc.) or a metal compound (e.g., chromous chloride, chromous acetate, etc.) in an acidic medium such as an inorganic acid (e.g., hydrochloric acid, etc.) or an organic acid (e.g., acetic acid, propionic acid, etc.), and catalytic reduction. The catalytic reduction can be carried out by any suitable conventional manner known in the art in the presence of a conventional catalyst such as palladium carbon or the like. Halogen substituted lower alkoxycarbonyl and 8-quinolyloxycarbonyl may be eliminated by treating the compound (IV) with a heavy metal (e.g., copper, zinc, etc.), and mesyl and tosyl may be eliminated by treating the compound (IV) with an alkali metal such as sodium metal in liquid ammonia. It is to be understood that any other conventional method for eliminating an amino-protective group may also be employed.

The temperature employed in the present reaction is not critical and may be suitably selected according to the kind of amino-protective group being used, the method of elimination employed, and similar considerations.

During the course of the reaction, depending upon the kind of elimination reaction used, some substituent(s) on the aryl group for R"₁ may be converted: for example, halogen may be converted into hydrogen; lower alkoxy, acyloxy, ar(lower)alkoxy, or lower alkylenedioxy may be converted into hydroxy; nitro, acylamino or ar(lower)alkylamino may be converted into amino; and lower alkenyl (as R"₁) may be also converted into lower alkyl. These possibilities are also included within the scope of the present invention.

The starting compound (IV) which itself is novel, can be prepared, for example, by reacting a compound of the formula:

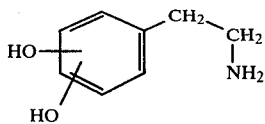

(II)

or a salt thereof, with an aldehyde compound of the formula:

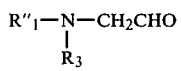

(III')

wherein R''$_1$ and R$_3$ are both as defined above, or are reactive equivalents thereof.

3. Another suitable alternative method is represented by the following scheme:

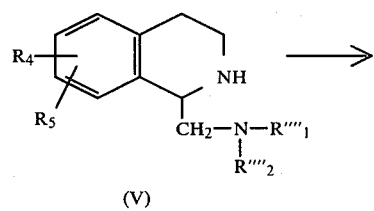

(V)

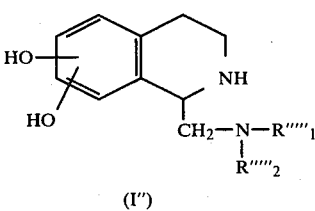

(I'')

wherein R$_4$ is a protected hydroxy, R$_5$ is hydroxy or a protected hydroxy, R'''''$_1$ and R'''''$_2$ are each hydrogen, lower alkyl, lower alkenyl, protective groups for amino, aryl or ar(lower)alkyl and R'''''$_1$ and R'''''$_2$ are each hydrogen, lower alkyl, lower alkenyl, aryl or ar(lower)alkyl, in which the aryl group and the aryl moiety of the ar(lower)alkyl for R'''''$_1$, R'''''$_2$, R'''''$_1$ and R'''''$_2$ may contain substituent(s) selected from the group consisting of halogen, lower alkoxy, amino, nitro, hydroxy, acyloxy, ar(lower)alkoxy, lower alkylenedioxy, halo(lower)alkyl, acylamino, ar(lower)alkylamino and aryl.

The present reaction may be carried out by subjecting the compound (V) or a salt thereof to an elimination reaction for the hydroxy-protective group(s).

Suitable hydroxy-protective groups referred to by the term "protected hydroxy" include the aforementioned acyl groups and further include lower alkyl (e.g., methyl, ethyl, propyl, isopropyl, etc.), allyl, ar(lower)alkyl such as phenyl(lower)alkyl (e.g., benzyl, phenethyl, etc.), trityl or the like, tetrahydropyranyl, lower alkoxy- or ar(lower)alkoxy(lower)alkyl (e.g., methoxymethyl, benzyloxymethyl, etc.), substituted phenylthio(e.g., 2-nitrophenylthio, 2,4-dinitrophenylthio, etc.), and the like, and also include the group formed when R$_4$ and R$_5$ are combined together to form lower alkylenedioxy (e.g., methylenedioxy, ethylenedioxy, etc.) when R$_4$ and R$_5$ are adjacent to each other. Suitable protective groups for hydroxy used in the present reaction are not limited to the groups mentioned above but include all conventional hydroxy-protective groups which are eliminable in the present reaction.

Suitable salts of the compound (V) include those mentioned for the compound (II).

The elimination reaction of the hydroxy-protective group(s) is carried out in a similar manner to that for the amino-protective group(s) mentioned above. Further, when R$_4$ and R$_5$ are combined together to form a lower alkylenedioxy group, hydrolysis using an acid is preferably employed. When the protective group(s) for hydroxy is lower alkyl, a method using an acid (e.g., hydrochloric acid or hydrobromic acid), boron trihalide (e.g., boron trichloride or boron tribromide), aluminum chloride, pyridine hydrohalide (e.g., pyridine hydrochloride, pyridine hydrobromide, etc.), lithium iodide, lithium tertiary-butyl sulfide or a mixture thereof, and the like, can be employed. When these are used in a liquid form, the reaction can be carried out without a solvent. Methylene chloride is often used as a solvent, but any other solvent which does not adversely affect the present reaction can be used.

The temperature used in the reaction is not critical. It can be suitably selected in accordance with the kind of protective group or elimination reaction, and the like being employed.

During the course of the reaction, by a kind of elimination reaction, occasionally lower alkenyl and ar(lower) alkyl (as R'''''$_1$ and R'''''$_2$) may be converted into lower alkyl and hydrogen, respectively. Also, some substituent(s) on the aryl and the ar(lower)alkyl groups (as R'''''$_1$ and R'''''$_2$) may be converted: for example, halogen may be converted into hydrogen; lower alkoxy, acyloxy, ar(lower)alkoxy or lower alkylenedioxy may be converted into hydroxy; and nitro, acylamino or ar(lower)alkylamino may be converted into amino. These possibilities are also included within the scope of the present invention.

The starting compound (V) which itself is novel, can be prepared, for example, (a) by reacting a compound of the formula:

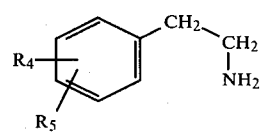

(II')

wherein R$_4$ and R$_5$ are each as defined above, or a salt thereof, with a compound of the formula:

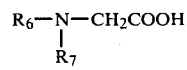

(VI)

wherein R$_6$ is hydrogen, lower alkyl, lower alkenyl, an aminoprotective group, aryl or ar(lower)alkyl and R$_7$ is lower alkyl, lower alkenyl, an amino-protective group, aryl or ar(lower)alkyl, in which the aryl and the aryl moiety of the ar(lower) alkyl for R$_6$ and R$_7$ may have substituent(s) selected from the group consisting of halogen, lower alkoxy, amino, nitro, hydroxy, acyloxy, ar(lower)alkoxy, lower alklenedioxy, halo(lower)alkyl, acylamino, ar(lower)alkylamino and aryl, or a reactive derivative thereof at the carboxy group, and treating the resulting compound of the formula:

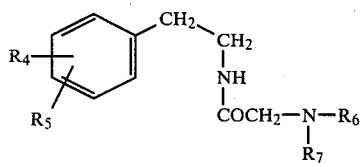 (VII)

wherein $R_4$, $R_5$, $R_6$ and $R_7$ are each as defined above, with a dehydrating agent, and thereafter reducing the resulting compound of the formula:

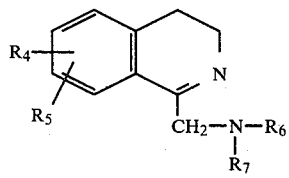 (VIII)

wherein $R_4$, $R_5$, $R_6$ and $R_7$ are each as defined above, or a salt thereof; or (b) reacting a compound of the formula:

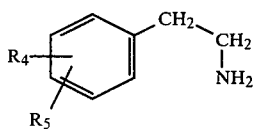 (II')

wherein $R_4$ and $R_5$ are each as defined above, or a salt thereof with a compound of the formula:

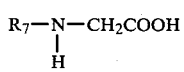
$$R_7-\underset{H}{N}-CH_2COOH \quad (VI')$$

wherein $R_7$ is as defined above, or a reactive derivative thereof at the carboxy group, and subjecting the resulting compound of the formula:

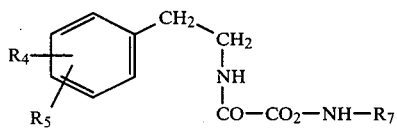 (VII')

wherein $R_4$, $R_5$ and $R_7$ are each as defined above, to a reaction for introducing an amino-protective group, and treating the resulting compound of the formula:

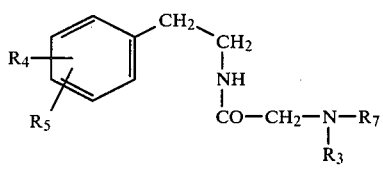 (VII")

wherein $R_3$, $R_4$, $R_5$, and $R_7$ are each as defined above, with a dehydrating agent, and thereafter reducing the resulting compound of the formula:

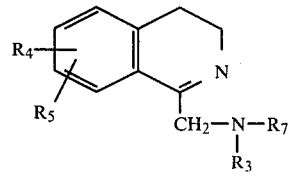 (VIII')

wherein $R_3$, $R_4$, $R_5$ and $R_7$ are each as defined above, or a salt thereof; or (c) subjecting the resulting compound obtained in process (b) of the formula:

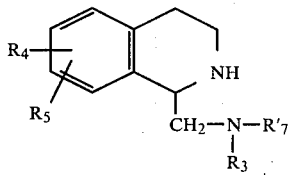 (IX)

wherein $R_3$, $R_4$ and $R_5$ are each as defined above, and $R'_7$ is lower alkyl, lower alkenyl, an amino-protective group, aryl or ar(lower)alkyl, in which the aryl and the aryl moiety of the ar(lower)alkyl may have substituent(s) selected from the group consisting of halogen, lower alkoxy, amino, nitro, hydroxy, acyloxy, ar(lower)alkoxy, lower alkylenedioxy, halo(lower) alkyl, acylamino, ar(lower)alkylamino and aryl, to a reaction eliminating the amino-protective groups(s).

The object compounds (I), (I') and (") obtained by the above methods may, if necessary, be converted into the pharmaceutically acceptable salt mentioned above.

The new 1,2,3,4-tetrahydroisoquinolines (I) of the present invention and the pharmaceutically acceptable salts thereof have a relaxant activity of smooth muscles, especially on vascular- and visceral-smooth muscles. Accordingly, they show vasodilating, intestinal-contraction inhibiting and bladder-contraction inhibiting activities, showing less bronchodilating activity, and are useful as vasodilating, intestinal-contraction inhibiting and bladder-contraction inhibiting agents. Thus, the compound (I) of the present invention and the pharmaceutically acceptable salts thereof can be used as a medicine for treating spasmodic disorder of visceral organs, e.g., colonic irritability, chronic cholecystitics and the like, in mammals.

The new 1,2,3,4-tetrahydroisoquinolines (I) and the pharmaceutically acceptable salts thereof can be administered by conventional methods, in conventional types of unit dosages or with conventional pharmaceutical carriers in order to produce a relaxing effect on smooth muscles.

Thus, they can be used in the form of conventional pharmaceutical preparations, wherein they are contained in admixture with a pharmaceutical organic or inorganic carrier material suitable for enteral or parenteral applications. Oral administration by the use of tablets, capsules or in a liquid form such as a suspension, solution or emulsion is particularly advantageous. When formed into tablets, conventional binding and disintegrating agents used in therapeutic unit dosages can be employed. Suitable binding agents include glucose, lactose, gum acacia, gelatin, mannitol, starch paste, magnesium trisilicate and talc. Suitable disintegrating agents include corn starch, keratin, colloidal silica and potato starch. When administered as liquids, conventional liquid carriers can be used.

The unit dosage or therapeutically effective quantity of the compounds (I) and the pharmaceutically acceptable salts thereof for human beings can vary over wide limits such as from 0.01 milligram to about 100 milligrams. The upper limit is limited only by the degree of the effect desired and economical considerations. For oral administration, it is preferred to employ from about 1 milligram to about 100 milligrams of the therapeutic agent per unit dosage. It is indicated from animal experiments that dosages from about 0.1 to about 10 milligrams administered orally three times daily as needed, will provide a preferred daily dosage. Of course, the suitable dosage of the particular therapeutic agent used can vary considerably dependent upon the age of the patient and the degree of therapeutic effect desired. Each unit dosage form of these novel therapeutic compounds can contain from about 0.5 to about 99.5% of the novel therapeutic agents by weight of the entire composition with the remainder comprising conventional pharmaceutical carriers. The term pharmaceutical carriers includes non-therapeutic materials which are conventionally used within a unit dosage and include fillers, diluents, binders, lubricants, disintegrating agents and solvents, i.e., the pure compounds, without the use of a pharmaceutical carrier. It is also possible to administer the new 1,2,3,4-tetrahydroisoquinolines (I) and the pharmaceutically acceptable salts thereof in the form of a mixture with other agents useful as relaxants for smooth muscles and especially vascular-smooth and visceral-smooth muscles.

The relaxing activity on smooth muscles of typical compounds which fall within the category of the compounds of the formula (I) of this invention can be illustrated by reference to a test in which the individual active ingredients employed were the following numbered compounds.

Compound No. 1

1-(p-Fluoroanilinomethyl)-6,7-dihydroxy-1,2,3,4-tetrahydroisoquinoline d-camphor-10-sulfonate Compound No. 2

1-(p-Chloroanilinomethyl)-6,7-dihydroxy-1,2,3,4-tetrahydroisoquinoline hydrochloride Compound No. 3

1-(p-Hydroxyanilinomethyl)-6,7-dihydroxy-1,2,3,4-tetrahydroisoquinoline dihydrochloride.

Test

Intestinal Motility in Dogs

Method: Mongrel dogs weighing 8 to 16 kg which were withheld from any food and water for 24 hours were anesthetized with a combination of urethane (1.5g/kg) and morphine (15 mg/kg). A balloon was placed at the jejunum of the dog, compressed at a pressure of 10 cm. $H_2O$ and connected to a strain gauge. Changes in the motility were principally recorded in terms of the amplitude of the movements, but the number of movements occurring were also taken into account. The maximum change in all the determinations served as the basis for calculations of the 50% inhibition dose ($ED_{50}$). Results are shown in the following table.

| Compound No. | $ED_{50}$ (g/kg) |
|---|---|
| 1 | 3 |
| 2 | 1.5 |
| 3 | 4 |

Having generally described the invention, a more complete understanding can be obtained by reference to certain specific examples, which are included for purposes of illustration only and are not intended to be limiting unless otherwise specified.

EXAMPLE 1

(A) N-benzyloxycarbonyl-p-toluidinoacetaldehyde diethyl acetal (6 g) and 3,4-dihydroxyphenethylamine hydrochloride (2.5 g) were added to a mixture of n-butyl alcohol (60 ml) and water (8.5 ml) and then the mixture was refluxed for 9.5 hours in a stream of nitrogen. In the course of the reaction, the above-mentioned acetal (0.6 g) was twice added to the mixture, after 5 hours and after 7.5 hours from the beginning of the reaction. The reaction mixture was concentrated and the residue was washed with ether and dissolved in hot water (300 ml). After the insoluble material was filtered off, the filtrate was washed with ethyl acetate and treated with activated charcoal. The aqueous layer was concentrated to dryness to give amorphous 1-(N-benzyloxycarbonyl-p-toluidinomethyl)-6,7-dihydroxy-1,2,3,4-tetrahydroisoquinoline hydrochloride (3.8 g), mp 125° C. (dec).

(B) N-benzyloxycarbonyl-p-fluoroanilinoacetaldehyde diethyl acetal (6 g) and 3,4-dihydroxyphenethylamine hydrochloride (2.5 g) were added to a mixture of n-butyl alcohol (60 ml) and water (8.5 ml). The mixture was then refluxed for 11 hours in a stream of nitrogen. In the course of the reaction, amounts of the above-mentioned acetal (0.6 g and 1.2 g) were added to the mixture after 4.5 hours and 6 hours, respectively, from the beginning of the reaction. The reaction mixture was concentrated to dryness and the residue was washed with ether and dissolved in water. The solution was washed with ether and concentrated to dryness to given amorphous 1-(N-benzyloxycarbonyl-p-fluoroanilinomethyl)-6,7-dihydroxy-1,2,3,4-tetrahydroisoquinoline hydrochloride (2.7 g), mp 122° C. (dec.).

(C) N-benzyloxycarbonyl-3,4,5-trimethoxyanilinoacetaldehyde diethyl acetal (21 g) and 3,4-dihydroxyphenethylamine hydrochloride (8.3 g) were added to a mixture of n-butyl alcohol (210 ml) and water (30 ml) and then the mixture was refluxed for 11 hours in a stream of nitrogen. In the course of the reaction, amounts of the above-mentioned acetal (2.1 g, 2.1 g and 4.2 g) were added to the mixture after 5 hours, 6 hours and 7 hours, respectively, from the beginning of the reaction, respectively. The reaction mixture was concentrated to dryness under reduced pressure and the residue was washed with ether and acetone to give 1-(N-benzyloxycarbonyl-3,4,5-trimethoxyanilinomethyl)-6,7-dihydroxy,1,2,3,4-tetrahydroisoquinoline hydrochloride (16.3 g). The product was recrystallized from a mixed solvent of ethanol and ether to give a pure product, mp 197° to 199° C. (dec).

(D) N-benzyloxycarbonyl-p-chloroanilinoacetaldehyde diethyl acetal (10 g) and 3,4-dihydoxyphenethylamine hydrochloride (4.2 g) were added to a mixture of n-butyl alcohol (100 ml) and water (14 ml) and then the mixture was refluxed for 4 hours. The above-mentioned acetal (1 g) was added to the mixture and the resultant mixture was refluxed for 4 hours. The reaction mixture was concentrated to dryness under reduced pressure and the residue was washed with ethyl acetate and collected by filtration. The crystals were recrystallized from a mixture of methanol and ether to give 1-(N-benzyloxycarbonyl-p-chloroanilinomethyl)-6,7-dihydroxy-1,2,3,4-tetrahydroisoquinoline hydrochloride (7.0 g), mp 210° to 212° C. (dec).

(E) N-ethoxycarbonyl-p-chloroanilinoacetaldehyde diethyl acetal (3.0 g) and 3,4-dihydroxyphenethylamine hydrochloride (1.5 g) were added to a mixture of n-butyl alcohol (30 ml), water (5 ml) and 10% hydrochloric acid (0.5 ml), and then the mixture was refluxed for 4 hours in a stream of nitrogen. Above mentioned acetal (0.8 g) was further added to the mixture and the resultant mixture was refluxed for 4 hours. The solvent was distilled off from the reaction mixture and the residue was washed with ethyl acetate and then recrystallized from water to give 1-(N-ethoxycarbonyl-p-chloroanilinomethyl)-6,7-dihydroxy-1,2,3,4-tetrahydroisoquinoline hydrochloride, mp 208° to 210° C. and mp 214° to 215° C. Analysis: Calcd. for $C_{19}H_{21}N_2O_4Cl.HCl.3/10H_2O$: C 54.50, H 5.44, N 6.69, Cl 16.93. Measured: C 54.29, H 5.57, N 6.70, Cl 16.69.

(F) N-benzyloxycarbonyl-N-isopropylaminoacetaldehyde diethyl acetal (9 g) and 3,4-dihydroxyphenethylamine hydrochloride (4.5 g) were added to a mixture of n-butyl alcohol (100 ml) and water (15 ml) and then the mixture was refluxed for 6 hours. The above-mentioned acetal (2 g) was added thereto and the resultant mixture was refluxed for 1.5 hours. The solvent was distilled off from the reaction mixture. To the residue was added a mixed solvent of isopropyl alcohol, methanol and ether. The crystals obtained was recrystallized from the same mixed solvent to give 1-(N-benzyloxycarbonyl-N-isopropylaminomethyl)-7,8-dihydroxy-1,2,3,4-tetrahydroisoquinoline hydrochloride (1.6 g), mp 200° to 205° C. (dec). The mother liquor was concentrated and allowed to stand to give 1-(N-benzyloxycarbonyl-N-isopropylaminomethyl)-6,7-dihydroxy-1,2,3,4-tetrahydroisoquiniline hydrochloride (4.4 g), colorless crystals, mp 207° to 210° C. (dec).

(G) N-benzyloxycarbonyl-m-fluoroanilinoacetaldehyde diethyl acetal (15 g) and 3,4-dihydroxyphenethylamine hydrochloride (5.75 g) were added to a mixture of n-butyl alcohol (150 ml) and water (20 ml) and then the mixture was refluxed for 11 hours in a stream of nitrogen. The reaction mixture was concentrated to dryness and the residue was in turn washed with ether and with a mixture of ether: ethyl acetate (2:1) and then crystallized with acetone. The crystals were collected by filtration to give 1-(N-benzyloxycarbonyl-m-fluoroanilinomethyl)-6,7-dihydroxy-1,2,3,4-tetrahydroisoquinoline hydrochloride (11.27 g), mp 184° to 186° C. (dec).

(H) N,N-diphenylaminoacetaldehyde diethyl acetal (3.5 g) and 3,4-dihydroxyphenethylamine hydrochloride (2.1 g) were added to a mixture of n-butyl alcohol (35 ml), water (5 ml) and conc. hydrochloric acid (2 drops) and then the mixture was refluxed for 6.5 hours in a stream of nitrogen. The reaction mixture was concentrated to dryness and the residue was washed with acetone and collected by filtration to recover the starting material, 3,4-dihydroxyphenethylamine (1.2 g). The filtrate was concentrated to give 1-(N,N-diphenylaminomethyl)6,7-dihydroxy-1,2,3,4-tetrahydroisoquinoline hydrochloride (1.5 g), oil.

(I) p-Chloroanilinoacetaldehyde diethyl acetal (486 mg) and 3,4-dihydroxyphenethylamine hydrochloride (378 mg) were added to a mixture of n-butyl alcohol (4 ml) and water (0.4 ml) and then the mixture was refluxed for 3.5 hours. The above-mentioned acetal (0.24 g) was further added thereto and the resultant mixture was refluxed for 3 hours. The reaction mixture was treated in a conventional manner to give 1-(p-chloroanilinomethyl)-6,7-dihydroxy-1,2,3,4-tetrahydroisoquinoline hydrochloride. This product was identified by thin-layer chromatography on silica gel [Developing solvent: (n-butyl alcohol:acetic acid:water=8:1:1)] with an authentic sample, mp 91° to 93° C., which was obtained by reacting 1-(N-benzyloxycarbonyl-p-chloroanilinomethyl)-6,7-dihydroxy-1,2,3,4-tetrahydroisoquinoline hydrochloride obtained in Example 1(D) with conc. hydrochloric acid and acetic acid.

(J) 3,4-Dihydroxyphenethylamine hydrochloride (41.4 g) and N-benzyloxycarbonyl-p-benzyloxyanilinoacetaldehyde diethyl acetal (147 g) were added to a mixture of n-butyl alcohol (1 l.) and water (130 ml) and then the mixture was refluxed overnight with stirring. N-Butyl alcohol was distilled from the reaction mixture under reduced pressure and the residue was pulverized by adding diisopropyl ether (500 ml). The powder was collected by filtration and dried by allowing it to stand overnight at ambient temperature to produce a powder (169 g). To the powder were added a saturated sodium bicarbonate aqueous solution (500 ml) and ethyl acetate (500 ml) and the mixture was shaken. The ethyl acetate layer was separated and the aqueous layer was further extracted with ethyl acetate (200 ml). Both ethyl acetate layers were mixed together, washed with a saturated sodium chloride aqueous solution (300 ml) and dried over magnesium sulfate. After drying, activated charcoal (3 g) was added to the solution and the mixture was filtered. The filtrate was concentrated under reduced pressure to give an oil (150 g). The oil was dissolved in ethyl acetate (600 ml) and p-toluenesulfonic acid monohydrate (50 g) was added thereto. The mixture was stirred at ambient temperature in order to precipitate crystals. After stirring for 2 hours, the precipitated crystals were collected by filtration, washed with ethyl acetate (100 ml) and dried by allowing them to stand overnight to give 1-(N-benzyloxycarbonyl-p-benzyloxyanilinomethyl)-6,7-dihydroxy-1,2,3,4-tetrahydroisoquinoline p-toluenesulfonate (70.6 g), mp 203° to 206° C. (dec). A portion of the crystals was recrystallized from 95% ethanol to give a pure product, mp 219°–220° C. (dec).

Analysis: Calcd. for $C_{38}H_{38}N_2O_8S$: C, 66.84; H, 5.61; N, 4.10. Measured: C, 66.96; H, 5.58; N, 4.07.

(K) A solution of 3,4-dihydroxyphenethylamine hydrochloride (2.17 g) and N-benzyloxycarbonylaminoacetaldehyde diethyl acetal (4.0 g) in a mixture of n-butyl alcohol (20 ml) and water (3.5 ml) was refluxed for 4.5 hours. After the reaction, the solvent was distilled off under reduced pressure. To the residue were added water (15 ml) and sodium acetate. A precipitating oil was separated from the aqueous layer and chloroform was added thereto. The mixture was allowed to stand to give crystals. The crystals were collected by filtration, washed with chloroform and recrystallized twice from a mixture of methanol and ether to give 1(N-benzyloxycarbonylaminomethyl)-6,7-dihydroxy-1,2,3,4-tetrahydroisoquinoline acetate (1.2 g), mp 158° to 162° C. (dec).

Analysis: Calcd. for $C_{20}H_{24}N_2O_6$: C, 61.84; H, 6.23; N 7.21. Meausred: C, 61.68; H, 6.16; N, 7.11.

Infrared Absorption Spectrum (Nujol) 1704, 1275 cm$^{-1}$.

Nuclear Magnetic Resonance Spectrum (d6-DMSO,δ), ppm 7.40 (5H, s), 6.60 (1H, s), 6.50 (1H, s), 5.12 (2H, s), 3.90 (1H, m), 3.22 (2H, m), 3.00 (2H, m), 2.63 (2H, m), 1.90 (3H, s).

The product was converted into its hydrochloride (oil) in a conventional manner.

(L) A mixture of N-acetyl-p-nitroanilinoacetaldehyde diethyl acetal (1 g), 3,4-dihydroxyphenethylamine hydrochloride (1 g), n-butyl alcohol (10 ml) and water (1.5 ml) was refluxed for 7 hours. In the course of the reaction, the above-mentioned acetal (2.5 g) was added to the mixture, twice in 0.5 g portions and five times in 0.3 g portions, one every hour. The reaction mixture was filtered and the filtrate was concentrated to dryness. The residue was pulverized by adding ether and the powder was collected by filtration, washed with ethyl acetate and water and dried to give 1-(p-nitroanilinomethyl)-6,7-dihydroxy-1,2,3,4-tetrahydroisoquinoline hydrochloride (1 g), mp 238° to 239° C. (dec).

Analysis: Calcd. for $C_{16}H_{17}N_3O_4 \cdot HCl \cdot H_2O$: C, 51.96; H, 5.45; N, 11.36. Measured: C, 52.56; H, 5.18; N, 11.24.

(M) The following compounds were obtained by a method similar to that used in Examples 1(A) through 1(L).

(1) 1-(p-Toluidinomethyl)-6,7-dihydroxy-1,2,3,4-tetrahydroisoquinoline dihydrobromide, mp 211° to 213° C.

(2) 1-(p-Fluoroanilinomethyl)-6,7-dihydroxy-1,2,3,4-tetrahydroisoquinoline d-camphor-10-sulfonate, mp 213° to 215° C.

(3) 1-(3,4,5-Trimethoxyanilinomethyl)-6,7-dihydroxy-1,2,3,4-tetrahydroisoquinoline hydrochloride, mp 232° to 225° C.

(4) 1-(N-isopropylaminomethyl)-6,7-dihydroxy-1,2,3,4-tetrahydrosioquinoline dihydrochloride, mp 268° to 270° C. (dec).

(5) 1-(N-isopropylaminomethyl)-7,8-dihydroxy-1,2,3,4-tetrahydroisoquinoline dihydrochloride, mp 255° to 258° C.

(6) 1-(m-Fluoroanilinomethyl)-6,7-dihydroxy-1,2,3,4-tetrahydroisoquinoline hydrochloride, powder.

(7) 1-Aminomethyl-6,7-dihydroxy-1,2,3,4-tetrahydroisoquinoline dihydrochloride, mp 142° to 147° C. (dec).

(8) 1-(p-Hydroxyanilinomethyl)-6,7-dihydroxy-1,2,3,4-tetrahydroisoquinoline dihydrochloride, mp 170° to 184° C. (dec).

(9) 1-(m-Trifluoromethylanilinomethyl)-6,7-dihydroxy-1,2,3,4-tetrahydroisoquinoline p-toluenesulfonate, mp 211° to 214° C.

(10) 1-(N-Benzyloxycarbonyl-n-trifluoromethylanilinomethyl)-6,7-dihydroxy-1,2,3,4-tetrahydroisoquinoline p-toluene-sulfonate, mp 218° to 220° C. (dec).

(11) 1-(3,4-Dichloroanilinomethyl)-6,7-dihydroxy-1,2,3,4-tetrahydroisoquinoline p-toluenesulfonate, mp 204° to 208° C. (dec).

(12) 1-(N-Benzyloxycarbonyl-3,4-dichloroanilinomethyl)-6,7-dihydroxy-1,2,3,4-tetrahydroisoquinoline p-toluenesulfonate, mp 227° to 229.5° C. (dec).

(13) 1-[N-(p-Chlorobenzyl)aminomethyl]-6,7-dihydroxy-1,2,3,4-tetrahydroisoquinoline dihydrochloride, mp 235° to 238° C. (dec).

Infrared Absorption Spectrum (Nujol) 1615, 1572 1450, 1375 cm$^{-1}$.

Nuclear Magnetic Resonance Spectrum (d6-DMSO,δ) ppm 7.60 (4H, m), 6.86 (1H, s), 6.62 (1H, s), 4.94 (1H, m), 4.22 (2H, broad s), 3.0–4.0 (4H, m), 2.70 (2H, m).

(14) 1-[N-Benzyloxycarbonyl-N-(p-chlorobenzyl)aminomethyl]-6,7-dihydroxy-1,2,3,4-tetrahydroisoquinoline hydrochloride, mp 214° to 217° C. (dec).

The following are other compounds suitable for preparation in this manner.

(15) 1-(p-Aminoanilinomethyl)-6,7-dihydroxy-1,2,3,4-tetrahydroisoquinoline dihydrochloride.

(16) 1-(p-Mesylaminoanilinomethyl)-6,7-dihydroxy-1,2,3,4-tetrahydroisoquinoline dihydrochloride.

(17) 1-(N-Acetyl-p-aminoanilinomethyl)-6,7-dihydroxy-1,2,3,4-tetrahydroisoquinoline hydrochloride.

(18) 1-(N-Acetyl-p-mesylaminoanilinomethyl)-6,7-dihydroxy-1,2,3,4-tetrahydroisoquinoline hydrochloride.

EXAMPLE 2

(A) A mixture of 1-(N-benzyloxycarbonyl-p-toluidinomethyl)-6,7-dihydroxy-1,2,3,4-tetrahydroisoquinoline hydrochloride (3 g), 48% hydrobromic acid (30 ml) and acetic acid (30 ml) was stirred for 3 hours at 80° C. The reaction mixture was concentrated to dryness and the residue was crystallized with acetone to give 1-(p-toluidinomethyl)-6,7-hydroxy-1,2,3,4-tetrahydroisoquinoline dihydrobromide (1.5 g). The product was recrystallized from a mixture of isopropyl alcohol and ether to give a pure product, mp 211° to 213° C.

Analysis: Calcd. for $C_{17}H_{20}N_2O_2 \cdot 2HBr$: C, 45.76; H, 4.97; N, 6.28; Br, 35.82. Measured: C, 45.56; H, 4.94; N, 6.23; Br, 35.55.

(B) A mixture of 1-(N-benzyloxycarbonyl-p-fluoroanilinomethyl)-6,7-dihydroxy-1,2,3,4-tetrahydroisoquinoline hydrochloride (4.6 g), conc. hydrochloric acid (46 ml) and acetic acid (46 ml) was refluxed for 2 hours. The reaction mixture was concentrated to dryness and the residue was dissolved in water and washed with a mixture of ether and ethyl acetate (1:1). The aqueous layer was treated with activated charcoal and concentrated to dryness to give 1-(p-fluoroanilinomethyl)-6,7-dihydroxy-1,2,3,4-tetrahydroisoquinoline hydrochloride (3.1 g). The product (2.5 g) was converted into its d-camphor-10-sulfonate in a conventional manner and the crystals obtained were recrystallized from water to give the d-camphor-10-sulfonate of the above-mentioned product, mp 213° to 215° C.

Analysis: Calcd. for $C_{26}H_{33}N_2O_6SF$: C, 59.98; H, 6.39; N, 5.38; S, 6.16. Measured: C, 59.67; H, 6.43; N, 5.32; S, 6.36.

(C) A mixture of 1-(N-benzyloxycarbonyl-3,4,5-trimethoxyanilinomethyl)-6,7-dihydroxy-1,2,3,4-tetrahydroisoquinoline hydrochloride (4.4 g), conc. hydrochloric acid (45 ml) and acetic acid (45 ml) was refluxed for 1.5 hours in a stream of nitrogen. The reaction mixture was concentrated to dryness and the residue was washed with ether and acetone and crystallized with methanol to give 1-(3,4,5-trimethoxyanilinomethyl)-6,7-dihydroxy-1,2,3,4-tetrahydroisoquinoline hydrochloride (2.3 g). The product was recrystallized from water to give a pure product, mp 223° to 225° C.

Analysis: Calcd. for $C_{19}H_{24}N_2O_5 \cdot HCl \cdot 1/7H_2O$: C, 57.13; H, 6.38; N, 7.01; Cl, 8.87. Measured: C, 57.39; H, 6.38; N, 6.99; Cl, 9.05.

(D) A mixture of 1(N-benzyloxycarbonyl-p-chloroanilinomethyl)-6,7-dihydroxy-1,2,3,4-tetrahydroisoquinoline hydrochloride (5.1 g), conc. hydrochloric acid (51 ml) and acetic acid (51 ml) was refluxed for 3 hours. The reaction mixture was concentrated to dryness under reduced pressure and the residue was dissolved in water. The aqueous layer was washed with ethyl acetate, treated with activated charcoal and concentrated to dryness to give crude 1-(p-chloroanilinomethyl)-6,7-dihydroxy-1,2,3,4-tetrahydroisoquinoline hydrochloride (2.8 g). The product was converted into its p-toluenesulfonate and then again converted into its hydrochloride by conventional techniques. The salt was recrystallized from water containing a small amount of hydrochloric acid to give pure 1-(p-chloroanilinomethyl)-6,7-dihydroxy-1,2,3,4-tetrahydroisoquinoline hydrochloride, mp 91° to 93° C.

Analysis: Calcd. for $C_{16}H_{17}N_2O_2Cl \cdot HCl$: C, 56.31; H, 5.32; N, 8.21; Cl, 20.78. Measured: C, 56.03; H, 5.26; N, 8.11; Cl, 20.73.

(E) A mixture of 1-(N-benzyloxycarbonyl-N-isopropylaminomethyl)-6,7-dihydroxy-1,2,3,4-tetrahydroisoquinoline hydrochloride (3.5 g), conc. hydrochloric acid (20 ml) and acetic acid (20 ml) was refluxed for 1 hour. The reaction mixture was concentrated to dryness under reduced pressure and the residue was crystallized with a mixture of acetone and water. The crystals were recrystallized from a mixture of methanol and ether to give 1-(N-isopropylaminomethyl)-6,7-dihydroxy-1,2,3,4-tetrahydroisoquinoline dihydrochloride (1.15 g), mp 268° to 270° C. (dec).

Analysis: Calcd. for $C_{13}H_{20}N_2O_2 \cdot 2HCl$: C, 50.49; H, 7.17; N, 9.06; Cl, 22.93. Measured: C, 50.44; H, 7.21; N, 8.94; Cl, 23.09.

(F) A mixture of 1-(N-benzyloxycarbonyl-N-isopropylaminomethyl)-7,8-dihydroxy-1,2,3,4-tetrahydroisoquinoline hydrochloride (1.1 g), acetic acid (11 ml) and conc. hydrochloric acid (11 ml) was refluxed for 1.5 hours. The reaction mixture was concentrated to dryness under reduced pressure and the residue was washed with acetone, followed by recrystallization from a mixture of methanol and ether to give 1-(N-isopropylaminomethyl)-7,8-dihydroxy-1,2,3,4-tetrahydroisoquinoline dihydrochloride, colorless crystals, mp 255° to 258° C.

Analysis: Calcd. for $C_{13}H_{20}N_2O_2 \cdot 2HCl$: C, 50.49; H, 7.17; N, 9.06; Cl, 22.93. Measured: C, 50.09; H, 7.03; N, 8.87; Cl, 22.60.

(G) A mixture of 1(N-benzyloxycarbonyl-m-fluoroanilinomethyl)-6,7-dihydroxy-1,2,3,4-tetrahydroisoquinoline hydrochloride (0.3 g), conc. hydrochloric acid (3 ml) and acetic acid (3 ml) was refluxed for 1.5 hours in a stream of nitrogen. The reaction mixture was concentrated and the residue was pulverized with ether to give 1-(m-fluoroanilinomethyl)-6,7-dihydroxy-1,2,3,4-tetrahydroisoquinoline hydrochloride (0.2 g), powder.

(H) A mixture of 1-(N-benzyloxycarbonylaminomethyl)-6,7-dihydroxy-1,2,3,4-tetrahydroisoquinoline hydrochloride (5.3 g), conc. hydrochloric acid (6 ml) and acetic acid (6 ml) was refluxed for 1 hour and 20 minutes. The reaction mixture was cooled and concentrated under reduced pressure. The residue was crystallized by adding methanol and acetone. The crystals were collected by filtration, washed with a mixture of methanol and acetone and recrystallized twice from a mixture of water, methanol and acetone to give 1-aminomethyl-6,7-dihydroxy-1,2,3,4-tetrahydroisoquinoline dihydrochloride (1.2 g), mp 142° to 147° C. (dec).

Infrared Absorption Spectrum (Nujol) 1604, 1552 $cm^{-1}$.

Nuclear Magnetic Resonance Spectrum ($d_6$-DMSO,$\delta$), ppm 6.73 (1H, s), 6.55 (1H, s), 4.80 (1H, m), 3.40 (4H, m), 2.82 (2H, m).

Analysis: Calcd. for $C_{10}H_{16}N_2O_2Cl_2$: C, 44.96; H, 6.04; N, 10.48; Cl, 26.54. Measured: C, 44.21; H, 5.90; N, 10.45; Cl, 26.77.

(I) To 1-(N-benzyloxycarbonyl-p-benzyloxyanilinomethyl)-6.7-dihydroxy-1,2,3,4-tetrahydroisoquinoline p-toluenesulfonate (10.0 g) was added a saturated sodium bicarbonate aqueous solution and then the mixture was extracted with ethyl acetate. The extract was washed with water, dried and the solvent was distilled off to give 1-(N-benzyloxycarbonyl-p-benzyloxyanilinomethyl)-6,7-dihydroxy-1,2,3,4-tetrahydroisoquinoline (8.2 g). To this residue (8.2 g) were added conc. hydrochloric acid (50 ml) and ethanol (50 ml) and the mixture was refluxed for 4 hours with stirring. The reaction mixture was concentrated to dryness under reduced pressure and the residue was pulverized with ether to give a powder of 1-(p-hydroxyanilinomethyl)-6,7-dihydroxy-1,2,3,4-tetrahydroisoquinoline dihydrochloride (5.8 g), mp 170° to 184° C. (dec).

Analysis: Calcd. for $C_{16}H_{18}N_2O_3 \cdot 2HCl \cdot H_2O$: C, 50.93; H, 5.88; N, 7.43. Measured: C, 51.09; H, 5.60; N, 7.15.

(J) The following compounds were obtained by a similar technique to that used in Examples 2(A) through 2(I).

(1) 1-(p-Nitroanilinomethyl)-6,7-dihydroxy-1,2,3,4-tetrahydroisoquinoline hydrochloride, mp 238° to 239° C. (dec).

(2) 1-(m-Trifluoromethylanilinomethyl)-6,7-dihydroxy-1,2,3,4-tetrahydroisoquinoline p-toluenesulfonate, mp 211° to 214° C.

(3) 1-(3,4-Dichloroanilinomethyl)-6,7-dihydroxy-1,2,3,4-tetrahydroisoquinoline p-toluenesulfonate, mp 204° to 208° C. (dec).

The following are other compounds suitable for preparation in this manner.

(4) 1-(p-Aminoanilinomethyl)-6,7-dihydroxy-1,2,3,4-tetrahydroisoquinoline dihydrochloride.

(5) 1-(p-Mesylaminoanilinomethyl)-6,7-dihydroxy-1,2,3,4-tetrahydroisoquinoline dihydrochloride.

PREPARATION OF THE STARTING COMPOUNDS (1)–(3)

(1)

1-(p-Toluidinomethyl)-6,7-dimethoxy-1,2,3,4-tetrahydroisoquinoline dihydrochloride (i)

N-[2-(3,4-Dimethoxyphenyl)ethyl]-2-(p-toluidino)acetamide 3,4-Dimethoxyphenethylamine (14.4 g) and p-toluidinoacetic acid (13.1 g) were heated for 1.5 hours at 190° C. in a stream of nitrogen. After cooling, the reaction mixture was dissolved in ethyl acetate and the solution was washed with a cooled 1 N sodium hydroxide solution and water and then dried. The solvent was distilled off and the oily residue was crystallized by adding ether to give N-[2-(3,4-dimethoxyphenyl)ethyl]-2-(p-toluidino)acetamide (18.6 g), mp 87° to 88.5° C.

(ii)
N-[2-(3,4-Dimethoxyphenyl)ethyl]-2-(N-benzyloxycarbonyl-p-toluidino)acetamide A mixture of N-[2-(3,4-dimethoxyphenyl)ethyl]-2-(p-toluidino)acetamide (3.6 g) and anhydrous potassium carbonate (2.5 g) was added to anhydrous dimethylformamide (25 ml). The mixture was vigorously stirred under ice cooling and to the solution was dropwise added over 20 minutes an anhydrous chloroform solution (5 ml) containing benzyl chloroformate (2.04 g). The reaction mixture was poured into ice-water and extracted with chloroform. The extract was washed with water, dried and the solvent was distilled off. The residue was crystallized by treating with ether to give N-[2-(3,4-dimethoxyphenyl)ethyl]-2-(N-benzyloxycarbonyl-p-toluidino)-acetamide (4.3 g), mp 81° to 85° C.

(iii)
1-(N-Benzyloxycarbonyl-p-toluidinomethyl)-6,7-dimethoxy-3,4-dihydroisoquinoline hydrochloride and phosphate N-[2-(3,4-Dimethoxyphenyl)ethyl]-2-(N-benzyloxycarbonyl-p-toluidino)acetamide (3.5 g) and phosphorus oxychloride (1.33 g) were added to anhydrous acetonitrile (45 ml) and the mixture was refluxed for 4 hours. The reaction mixture was concentrated to dryness under reduced pressure to give a crude mixture of hydrochloride and phosphate of 1-(N-benzyloxycarbonyl-p-toluidinomethyl)-6,7-dimethoxy-3,4-dihydroisoquinoline (4.6 g).

(iv)
1-(N-Benzyloxycarbonyl-p-toluidinomethyl)-6,7-dimethoxy-1,2,3,4-tetrahydroisoquinoline hydrochloride A mixture of hydrochloride and phosphate of 1-(N-benzyloxycarbonyl-p-toluidinomethyl)-6,7-dimethoxy-3,4-dihydroisoquinoline (4.6 g) was dissolved in 99% ethanol (45 ml). To the solution was added sodium borohydride (0.8 g) with stirring under ice cooling, and the mixture was stirred for 1.5 hours. The reaction mixture was concentrated to dryness under reduced pressure and to the residue was added water. The mixture was saturated with sodium chloride and extracted with ethyl acetate. The extract was dried and the solvent was distilled off. The oil obtained was treated with ethanol containing hydrochloric acid to give 1-(N-benzyloxycarbonyl-p-toluidinomethyl)-6,7-dimethoxy-1,2,3,4-tetrahydroisoquinoline hydrochloride (2.3 g), mp 189° to 190° C.

(v)
1-(p-Toluidinomethyl)-6,7-dimethoxy-1,2,3,4-tetrahydroisoquinoline dihydrochloride A mixture of 1-(N-benzyloxycarbonyl-p-toluidinomethyl)-6,7-dimethoxy-1,2,3,4-tetrahydroisoquinoline hydrochloride (470 mg), acetic acid (4.7 ml) and conc. hydrochloric acid (4.7 ml) was heated for 1 hour at 100° C. The reaction mixture was concentrated to dryness under reduced pressure and the residue was dissolved in methanol. To the solution was added ethyl acetate and the precipitating crystals were collected by filtration to give 1-(p-toluidinomethyl)-6,7-dimethoxy-1,2,3,4-tetrahydroisoquinoline dihydrochloride (270 mg), mp 180° to 184° C.

(2)
1-(N-Benzyloxycarbonyl-p-chloroanilinomethyl)-6,7-dibenzyloxy-1,2,3,4-tetrahydroisoquinoline hydrochloride (i)
N-[2-(3,4-Dibenzyloxyphenyl)ethyl]-2-(p-chloroanilino)acetamide A mixture of 3,4-dibenzyloxyphenethylamine (36.2 g) and p-chloroanilinoacetic acid (20 g) was stirred for 3 hours at 190° C. The reaction mixture was dissolved in benzene. The solution was washed with a diluted potassium carbonate aqueous solution and dried. The solvent was distilled off from the benzene solution and the residue obtained was purified by column chromatography on silica gel to give N-[2-(3,4-dibenzyloxyphenyl)ethyl]-2-(p-chloroanilino)acetamide (27.2 g), mp 121° C.

(ii)
N-[2-(3,4-Dibenzyloxyphenyl)ethyl]-2-(N-benzyloxycarbonyl-p-chloroanilino)acetamide A mixture of N-[2-(3,4-dibenzyloxyphenyl)ethyl]-2-(p-chloroanilino(acetamide (13.4 g) and anhydrous potassium carbonate (7.5 g) was added to anhydrous dimethylformamide (100 ml). To the solution was added dropwise over 30 minutes benzyl chloroformate (9.2 g) with stirring and ice-cooling. The reaction mixture was poured into ice-water and extracted with ethyl acetate. The extract was washed with water and dried. The solvent was distilled off from the solution and the residue obtained was recrystallized from a mixture of benzene and petroleum ether to give N-[2-(3,4-dibenzyloxyphenyl)ethyl]-2-(N-benzyloxycarbonyl-p-chloroanilino)acetamide (9.0 g) mp 114° to 116.5° C.

(iii)
1-(N-Benzyloxycarbonyl-p-chloroanilinomethyl)-6,7-dibenzyloxy-3,4-dihydroisoquinoline A mixture of N-[2-(3,4-dibenzyloxyphenyl)ethyl]-2-(N-benzyloxycarbonyl-p-chloroanilino)acetamide (7.3 g), phosphorus oxychloride (2.3 g) and anhydrous benzene (73 ml) was refluxed for four hours. The reaction mixture was concentrated to dryness under reduced pressure and to the residue was added a diluted aqueous ammonia solution, and then the mixture was extracted with ethyl acetate. The extract was washed with water and dried, and the solvent was distilled off to give 1-(N-benzyloxycarbonyl-p-chloroanilinomethyl)-6,7-dibenzyloxy-3,4-dihydroisoquinoline (7.0 g).

(iv)
1-(N-Benzyloxycarbonyl-p-chloroanilinomethyl)-6,7-dibenzyloxy-1,2,3,4-tetrahydroisoquinoline hydrochloride 1-(N-Benzyloxycarbonyl-p-chloroanilinomethyl)-6,7-dibenzyloxy-3,4-dihydroisoquinoline (7.0 g) was added to 99% ethanol (160 ml) and to the solution was gradually added sodium borohydride (2.2 g) under ice cooling. The reaction temperature of the mixture was elevated to ambient temperature and the mixture was stirred for 3 hours. An insoluble material was filtered off from the reaction mixture and the filtrate was concentrated under reduced pressure. After water was added to the residue, the mixture was extracted with ethyl acetate. The extract was washed with water and dried. The solvent was distilled off from the solution and the residue was subjected to column chromatography on silica gel, washed with benzene and eluted with a mixture of chloroform and ethyl acetate. The eluate was concentrated and the residue was treated with ethanol containing hydrochloric acid. The crystals obtained were recrystallized from a mixture of 99% ethanol and ether to give 1-(N-benzyloxycarbonyl-p-chloroanilinomethyl)-6,7-dibenzyloxy-1,2,3,4-tetrahydroisoquinoline hydrochloride (1.4 g), mp 139° to 142° C.

(3)
1-(N,N-Diphenylaminomethyl)-6,7-dimethoxy-1,2,3,4-tetrahydroisoquinoline (i)
N-[2-(3,4-Dimethoxyphenyl)ethyl]-2-(N,N-diphenylamino)acetamide 3,4-Dimethoxyphenethylamine (8.05 g) and N,N-diphenylglycine (10 g) were heated for 2 hours at 190° C. After cooling, the reaction mixture was dissolved in ethylacetate. The resulting solution was washed with a 5% sodium bicarbonate aqueous solution and water and then dried. The solvent was distilled off from the solution to give crystals of N-[2-(3,4-dimethoxyphenyl)ethyl]-2-(N,N-diphenylamino)acetamide (11.5 g), mp 88° to 93° C.

(ii)
1-(N,N-Diphenylaminomethyl)-6,7-dimethoxy-3,4-dihydroisoquinoline hydrochloride and phosphate A mixture of N-[2-(3,4-dimethoxyphenyl)ethyl]-2-(N,N-diphenylamino)acetamide (2 g), phosphorus oxychloride (0.79 g) and anhydrous acetonitrile (25 ml) was refluxed for 4 hours. Acetonitrile was removed from the reaction mixture and phosphorus oxychloride was completely removed from the residue by adding dry benzene to the residue and thereafter removing it to give a mixture of 1-(N,N-diphenylaminomethyl)-6,7-dimethoxy-3,4-dihydroisoquinoline hydrochloride and phosphate, amorphous form.

(iii)
1-(N,N-Diphenylaminomethyl)-6,7-dimethoxy-1,2,3,4-tetrahydroisoquinoline

To the amorpohous substance obtained in the above preparation of compound (3) (ii) was added 99% ethanol (30 ml) and to the solution was added sodium borohydride (0.4 g) with stirring and ice cooling. The mixture was stirred for 16 hours at ambient temperature. The precipitate was filtered off and the filtrate was concentrated. To the residue were added ethyl acetate and water, and the mixture was sufficiently shaken. The ethyl acetate layer was separated, washed with water, dried and the solvent was distilled off. The residual oil (1.3 g) was purified by column chromatography on silica gel (50 g) using chloroform as the developing solvent to give 1-(N,N-diphenylaminomethyl)-6,7-dimethoxy-1,2,3,4-tetrahydroisoquinoline (0.82 g).

EXAMPLE 3

(A) 1-(p-Toluidinomethyl)-6,7-dimethoxy-1,2,3,4-tetrahydroisoquinoline dihydrochloride (260 mg) was converted into the free amine compound by conventional methods. The amine compound was dissolved in anhydrous dichloromethane (10 ml) and to the solution was dropwise added at −50° C. anhydrous dichloromethane (5 ml) containing boron tribromide (340 mg). The mixture was stirred for 14 hours at the same temperature and the reaction temperature was gradually elevated to 8° C. The reaction mixture was concentrated to dryness under reduced pressure and the residue obtained was crystallized with acetone. The crystals were further recrystallized from a mixture of isopropyl alcohol and ether to give 1-(p-toluidinomethyl)-6,7-dihydroxy-1,2,3,4-tetrahydroisoquinoline dihydrobromide, mp 211° to 213° C. The product was identified by means of comparison with an authentic sample prepared by another process by its infrared absorption spectrum and nuclear magnetic resonance spectrum.

(B) A mixture of 1-(N-benzyloxycarbonyl-p-chloroanilinomethyl)-6,7-dibenzyloxy-1,2,3,4-tetrahydroisoquinoline hydrochloride (1.1 g), acetic acid (11 ml) and conc. hydrochloric acid (11 ml) was heated for 2 hours at 100° C. The reaction mixture was concentrated to dryness under reduced pressure and the residue was washed with ethyl acetate and ether and pulverized to give crude 1-(p-chloroanilinomethyl)-6,7-dihydroxy-1,2,3,4-tetrahydroisoquinoline hydrochloride. The product was converted into its p-toluenesulfonate and then again converted into its hydrochloride to give a pure product, mp 91° to 93° C. The product was identified by means of comparison with an authentic sample prepared by another process by its infrared absorption spectrum and nuclear magnetic resonance spectrum.

(C) To a solution of 1-(N,N-diphenylaminomethyl)-6,7-dimethoxy-1,2,3,4-tetrahydroisoquinoline (0.38 g) in anhydrous dichloromethane (15 ml) was dropwise added a solution of boron tribromide (0.75 g) in anhydrous dichloromethane (5 ml) at −60° C. with stirring. The mixture was stirred for 2.5 hours at the same temperature and the reaction temperature was elevated to ambient temperature over 19 hours. Dichloromethane was removed and to the residue were added methanol and a small amount of water. The mixture was warmed and concentrated to dryness. The residue was crystallized with a mixture of acetone and ether and the crystals were collected by filtration to give 1-(N,N-diphenylaminomethyl)-6,7-dihydroxy-1,2,3,4-tetrahydroisoquinoline hydrobromide (0.33 g).

(D) The following compounds were obtained according to similar techniques used in Examples 3(A) through 3(C).

(1) 1-(p-Fluoroanilinomethyl)-6,7-dihydroxy-1,2,3,4-tetrahydroisoquinoline d-camphor-10-sulfonate, mp 213° to 215° C.

(2) 1-(3,4,5-Trimethoxyanilinomethyl)-6,7-dihydroxy-1,2,3,4-tetrahydroisoquinoline hydrochloride, mp 223° to 225° C.

(3) 1-(N-Isopropylaminomethyl)-6,7-dihydroxy-1,2,3,4-tetrahydroisoquinoline dihydrochloride, mp 268° to 270° C. (dec).

(4) 1-(N-Isopropylaminomethyl)-7,8-dihydroxy-1,2,3,4-tetrahydroisoquinoline dihydrochloride, mp 255° to 258° C.

(5) 1-(m-Fluoroanilinomethyl)-6,7-dihydroxy-1,2,3,4-tetrahydroisoquinoline hydrochloride, powder.

(6) 1-Aminoethyl-6,7-dihydroxy-1,2,3,4-tetrahydroisoquinoline dihydrochloride, mp 142° to 147° C. (dec).

(7) 1-(p-Hydroxyanilinomethyl)-6,7-dihydroxy-1,2,3,4-tetrahydroiosquinoline dihydrochloride, mp 170° to 184° C. (dec).

(8) 1-(p-Nitroanilinomethyl)-6,7-dihydroxy-1,2,3,4-tetrahydroisoquinoline hydrochloride, mp 238° to 239° C. (dec).

(9) 1-(m-Trifluoromethylanilinomethyl)-6,7-dihydroxy-1,2,3,4-tetrahydroisoquinoline p-toluenesulfonate, mp 211° to 214° C.

(10) 1-(3,4-Dichloroanilinomethyl)-6,7-dihydroxy-1,2,3,4-tetrahydroisoquinoline p-toluenesulfonate, mp 204° to 208° C. (dec).

(11) 1-[N-(p-Chlorobenzyl)aminomethyl]-6,7-dihydroxy-1,2,3,4-tetrahydroisoquinoline dihydrochloride, mp 235° to 238° C. (dec).

Infrared Absorption Spectrum (Nujol) 1615, 1572, 1450, 1375 cm$^{-1}$.

Nuclear Magnetic Resonance Spectrum (d$_6$-DMSO,δ), ppm 7.60 (4H, m), 6.86 (1H, s), 6.62 (1H, s), 4.94 (1H, m), 4.22 (2H, broad s), 3.0–4.0 (4H, m), 2.70 (2H, m).

The following are other compounds suitable for preparation in this manner.

(12) 1-(p-Aminoanilinomethyl)-6,7-dihydroxy-1,2,3,4-tetrahydroisoquinoline dihydrochloride.

(13) 1-(p-Mesylaminoanilinomethyl)-6,7-dihydroxy-1,2,3,4-tetrahydroisoquinoline dihydrochloride.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. 1,2,3,4-Tetrahydroisoquinolines of the formula:

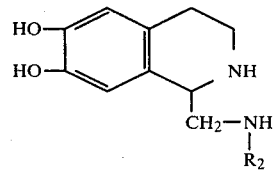

wherein R$_2$ is phenyl containing 1 to 3 lower alkoxy substituents, and pharmaceutically acceptable salts thereof.

2. The compounds of claim 1 wherein R$_2$ is 3,4,5-tri(lower)alkoxyphenyl.

3. The compounds of claim 1 wherein R$_2$ is 3,4,5-trimethoxyphenyl.

4. A pharmaceutical muscle relaxant composition for mammals comprising a pharmaceutically effective amount of a compound of claim 1 admixed with a pharmaceutically acceptable, substantially non-toxic carrier or excipient.

5. A method of relaxing smooth muscles in mammals which comprises administering an amount of a compound of claim 1 sufficient for effectively relaxing said smooth muscles.

* * * * *